(12) United States Patent
Bousse et al.

(10) Patent No.: US 6,803,568 B2
(45) Date of Patent: Oct. 12, 2004

(54) MULTI-CHANNEL MICROFLUIDIC CHIP FOR ELECTROSPRAY IONIZATION

(75) Inventors: Luc Bousse, Los Altos, CA (US); John T. Stults, Redwood City, CA (US)

(73) Assignee: Predicant Biosciences, Inc., South San Francisco, CA (US)

( * ) Notice: Subject to any disclaimer, the term of this patent is extended or adjusted under 35 U.S.C. 154(b) by 0 days.

(21) Appl. No.: 10/649,350

(22) Filed: Aug. 26, 2003

(65) Prior Publication Data

US 2004/0113068 A1 Jun. 17, 2004

(30) Foreign Application Priority Data

Sep. 19, 2001 (DE) .......................................... 101 46 286

(51) Int. Cl.[7] .......................... H01J 49/04; B01D 59/44
(52) U.S. Cl. ...................... 250/288; 250/282; 250/281; 250/285; 250/428
(58) Field of Search ............................... 250/288, 282, 250/281, 285, 428

(56) References Cited

U.S. PATENT DOCUMENTS

| | | | |
|---|---|---|---|
| 5,969,353 A | 10/1999 | Hsieh et al. | |
| 6,176,962 B1 | 1/2001 | Soane et al. | |
| 6,459,080 B1 | 10/2002 | Yin et al. | |
| 6,465,776 B1 * | 10/2002 | Moini et al. | 250/285 |
| 6,481,648 B1 | 11/2002 | Zimmermann et al. | |
| 6,541,768 B2 | 4/2003 | Andrien, Jr. et al. | |
| 2003/0089605 A1 * | 5/2003 | Timperman | 204/450 |

OTHER PUBLICATIONS

Kameoka, Jun, et al. "An Electrospray Ionization Source for Integration with Microfluidics". *Analytical Chemistry*, (Nov. 15, 2002), 5897–5901, vol. 74, No. 22.

Xue, Qifeng, et al. "Multichannel Microchip Electrospray Mass Spectrometry". *Analytical Chemistry*, (Feb. 1, 1997), 426–430, vol. 69, No. 3.

Gobry, Véronique, et al. "Microfabricated polymer injector for direct mass spectrometry coupling". *Proteomics*, (2002), 405–412, vol. 2.

Ramsey, R.S., et al. "Generating Electrospray from Microchip Devices Using Electroosmotic Pumping". *Analytical Chemistry*, (Mar. 15, 1997), 1174–1178, vol. 69, No. 6.

Rohner, Tatiana, et al. "Polymer Microspray with an Integrated Thick–Film Microelectrode". *Analytical Chemistry*, (Nov. 15, 2001), 5353–5357, vol. 73, No. 22.

Lin, Yuehe, et al. "Microfluidic Devices on Polymer Substrates for Bioanalytical Applications". *Pacific Northwest National Laboratory*, (1999), Richland, WA, USA.

Zhang, et al. "Microfabricated Devices for Capillary Electrophoresis–Electrospray Mass Spectrometry", *Anal. Chem.*, (Aug. 1, 1999), 3258–3264, vol. 71, No. 15.

(List continued on next page.)

*Primary Examiner*—Nikita Wells
(74) *Attorney, Agent, or Firm*—Wilson Sonsini Goodrich & Rosati (57) ABSTRACT

A microfluidic chip formed with multiple fluid channels terminating at a common electrospray ionization tip for mass spectrometric analysis. The fluid channels may be formed within a substrate plate that are in fluid communication with corresponding reservoirs. The electrospray tip can be formed along a defined portion of the substrate plate, wherein the electrospray tip includes an open-tip region at which the fluid channels converge. A top laminate plate may substantially enclose most portions of the fluid channels formed in the bottom polymer plate except for the open-tip region. Another aspect of the invention provides methods for conducting mass spectrometric analysis of multiple samples flowing through individual fluid channels in a single microfluidic chip that is formed with a convergent electrospray tip. The convergent electrospray tip includes an open or exposed distal pointed tip region.

12 Claims, 9 Drawing Sheets

OTHER PUBLICATIONS

Geromanos, S. et al., InJection adaptable Fine Ionization Source ('JaFIS') for Continuous Flow Nano–electrospray, *Rapid Commun. Mass Spectrom* (1998) vol. 12, pp. 551–556.

Geromanos, S. et al., Tuning of an Electrospray Ionization Source for Maximum Peptide–Ion Transmission into a Mass Spectrometer, *Anal. Chem.* (2000) vol. 72, No. 4, pp. 777–790.

* cited by examiner

MULTI-CHANNEL MICROFLUIDIC CHIP FOR ELECTROSPRAY IONIZATION

FIELD OF THE INVENTION

The invention relates to microfluidic chips for electrospray ionization applications. More particularly, the invention relates to improved electrospray ionization tips for mass spectrometric analysis.

BACKGROUND OF THE INVENTION

Electrospray ionization is used to produce ions for mass spectrometry analysis including ions that are derived from relatively large complex molecules such as proteins and nucleic acid molecules. During the electrospray ionization procedure, a sample solution is exposed to an electrical field that charges the surface of the liquid and emerges from an electrospray tip or needle. A spray of finely dispersed charged droplets is thereby generated that is suitable for analysis by a mass spectrometer. The need for conducting high-throughput analysis of relatively small biological samples has led to the development of microfluidic chip devices for electrospray ionization applications.

Microfluidic chips are often constructed using well known techniques employed in the semiconductor industry such as photolithography, wet chemical etching, and thin film deposition. These devices conveniently support the separation and analysis of sample sizes that are as small as a few nanoliters or less. In general, these chips are formed with a number of microchannels that are connected to a variety of reservoirs containing fluid materials. The fluid materials are driven or displaced within these microchannels throughout the chip using electrokinetic forces, pumps and/or other driving mechanisms. The microfluidic devices available today can conveniently provide mixing, separation, and analysis of fluid samples within an integrated system that is formed on a single chip.

There are numerous design alternatives to choose from when constructing an interface for microfluidic chips and electrospray ionization mass spectrometers. Some electrospray ionization interfaces include microfluidic chips that attempt to spray charged fluid droplets directly from the edge of the chip. But the accompanying solvent is known to wet much of the edge surface of the chip so as not to offer a high-stability spray for many applications. Other attempts to spray ionized particles directly from the edge of a microfluidic chip edge therefore rely on the formation of a hydrophobic surface that can yield improved spray results; however, even that often proves to be insufficiently stable. At the same time, adequate results can be also achieved with other chip devices that incorporate fused silica capillary needles or micromachined or molded tips. In particular, some recent electrospray ionization designs incorporate small silicon etched emitters positioned on the edge of a microfluidic chip. While it is possible to generate a relatively stable ionization spray for mass spectrometric analysis with some of these microfluidic devices today, they generally require apparatus that is relatively impractical and economically unfeasible for mass production.

A high performance electrospray ionization device is therefore needed for mass spectrometry applications that can be economically produced using large scale manufacturing processes.

SUMMARY OF THE INVENTION

The invention provides methods and apparatus related to microfluidic chips and electrospray ionization applications. Various aspects of the invention can be appreciated individually or collectively to provide an effective interface for microfluidic systems and mass spectrometers or other analytical devices.

A preferable embodiment of the invention provides microfluidic chips that are formed with individual fluid channels. These fluid channels extend through the body of the microfluidic chip and converge at a common distal tip region. The distal tip region includes an open-ended distal tip formed along a defined surface of a microfluidic chip body. The microfluidic chip may be constructed from a pair of polymer plates in which the converging channels run through and lead up to the distal tip region. The microfluidic chip can be also formed with multiple but separate channels that supply fluids such as samples and sheath flow solutions to a single common electrospray tip.

In accordance with another embodiment of the invention, a recessed electrospray ionization tip is provided that is formed along a defined edge of a microfluidic chip. The electrospray device may include a separately formed tip constructed from a shaped thin-film that is bonded to and in between a pair of polymer layers. The separately formed tip may be formed with an exposed distal tip region at which multiple fluid channels converge. The tip may further include fluid channels that are respectively aligned with corresponding fluid channels that are embossed or otherwise formed within the microfluidic chip.

The invention further provides single-use disposable microfluidic chips that are reliable, reproducible and easy-to-use. These microfluidic chips may be selected for sample separation and electrospray ionization processes utilizing electrospray emitters that are formed as an integral part of the chip. These embodiments of the invention reflect a chip design that provides an economical and effective solution that can be reproduced on a large scale production. Many microfluidic chips can be fabricated in batch quantities thus reducing the number of time-consuming steps in forming electrospray emitters and tips.

Another aspect of the invention provides methods of manufacturing microfluidic devices with separately formed ESI emitters. The microfluidic devices may be readily manufacturable following a mass production molding process. Many individual fluid devices may be fabricated at the same time using techniques similar to the manufacture of semiconductor chips for microprocessors. A metal-coated thin film polymer may be separately formed and bonded to polymer plates which are later separated into individual microfluidic devices by cutting apparatus. These and other embodiments of the invention provide convenient fabrication methods for economically manufacturing microfluidic devices for electrospray ionization applications.

Other goals and advantages of the invention will be further appreciated and understood when considered in conjunction with the following description and accompanying drawings. While the following description may contain specific details describing particular embodiments of the invention, this should not be construed as limitations to the scope of the invention but rather as an exemplification of preferable embodiments. For each aspect of the invention, many variations are possible as suggested herein that are known to those of ordinary skill in the art. A variety of changes and modifications can be made within the scope of the invention without departing from the spirit thereof.

BRIEF DESCRIPTION OF THE FIGURES

The illustrations included within this specification describe many of the advantages and features of the invention. It shall be understood that similar reference numerals and characters noted within the illustrations herein may designate the same or like features of the invention. The illustrations and features depicted herein are not necessarily drawn to scale.

DETAILED DESCRIPTION OF THE INVENTION

Figure 1:
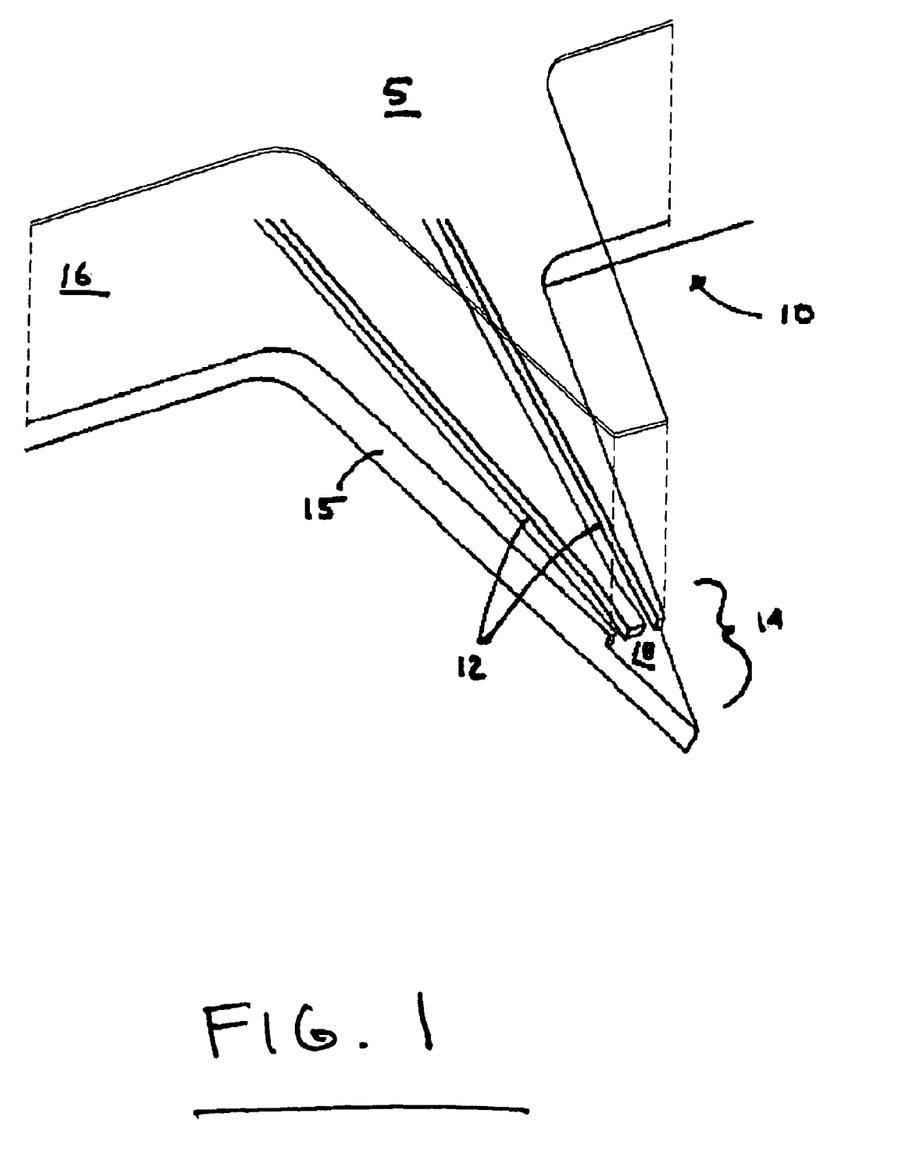
FIG. 1 is an enlarged perspective view of a microfluidic chip that is formed with a tip and a pair of fluid channels converging at a distal tip region in accordance with the invention.

FIG. 1 illustrates a microfluidic chip 10 for electrospray ionization (ESI) applications that is formed with multiple fluid channels 12 converging at a distal tip region 14. The fluid channels 12 may be formed on a substrate layer 16 of the chip 10 that is composed of glass, quartz, ceramic, silicon, silica, silicon dioxide or other suitable material such as a polymer, copolymer, elastomer or a variety of commonly used plastics. The channels 12 can be created using a variety of methods, such as conventional semiconductor processing methods including photolithographically masked wet-etching and photolithographically masked plasma-etching, or other processing techniques including embossing, molding, injection molding, photoablating, micromachining, laser cutting, milling, and die cutting. A variety of channel patterns and configurations may be also selected for the channels, including channels having a substantially rectangular, trapezoidal, triangular, or D-shaped cross-section. For example, these channels may be produced with an anisotropically etched silicon master having a trapezoidal or triangular cross-section. A channel having a D-shaped cross-section may be formed alternatively following isotropic etching processes. The pair of channels 12 formed on the substrate layer 16 can run relatively non-parallel as shown with respect to each other which substantially converge at the distal tip region 14. A thin film laminate 5 encloses the channels 12 which can be bonded to the substrate layer 16. The thin film 5 is formed so as to terminate at the end of the channels 12 at the distal tip region 14. The distal tip region 14 of the ESI tip 15 may be formed with an open-ended construction where different fluids can emerge or emit therefrom for analysis by a mass spectrometer or other analytical apparatus.

There are numerous advantages in forming multiple channels that meet at a single tip on a microfluidic device. For example, this type of construction may enable analysis of several fluid samples in sequence on the same ESI tip. A calibration solution may be selected among these fluids to adjust the operating conditions of the ESI tip before the sample under test is analyzed. The calibration solution can be used in automating this process of adjusting and optimizing the positioning or conditions of the electrospray, including the physical location of the tip relative to the mass spectrometry instrument and the applied voltage. A calibration solution may also be provided to calibrate the mass spectrometer for mass accuracy, and thereby improve the performance of the instrument. An advantage of carrying out an optimization process on the same tip to be actually used for the samples under test is that the need for and repositioning of another tip may be avoided. Moreover, the ESI tips may each have a slightly different geometry and location relative to the mass spectrometer in some instances that would require additional alignment and repeated optimization. These and other drawbacks are avoided with the microfluidic chips provided in accordance with this aspect of the invention.

The electrospray devices described herein preferably include emitter tips 15 having an open-tip region 18 with converging multiple fluid channels 12. In accordance with this embodiment of the invention, ESI tips 15 do not have an enclosed distal tip region 18 and can thus allow fluids to flow along the external surface thereof. A microfluidic chip 10 formed with an open-tip emitter as described herein possesses another distinctive feature in that the multiple channels 12 leading up to this distal tip area intersect at the tip 15 instead of connecting within the body of the chip. By connecting the converging channels 12 at the open distal end 18 of the spray tip 15, the fluid movement within a single channel will not disturb flow in other channels within the chip body. For instance, the application of pressure to a calibration solution source will induce flow within the respective internal channels, and eventually out of the ESI tip. But this separate calibration solution flow does not interfere with a separate sample channel or other fluid channel formed within the same microfluidic chip. For certain applications where multiple channels leading to a single distal tip are used to supply a series of distinct samples in a sequential manner one after the other, the invention provided herein eliminates or reduces the possibility of cross-contamination between fluid samples. The distinct multiple channels are not in fluid communication with each other within the chip or otherwise connected, but rather they lead to and converge at the common tip structure. In this manner, the samples under test and other solutions are not mixed or become cross-contaminated with each other within in the microfluidic device itself. Accordingly, each fluid can be independently electrosprayed from the same open tip structure outside and beyond the closed channels of the device body into a mass spectrometer for testing and analysis.

The substrate portions 16 for the edge-emitting ESI tips described herein may be integrally formed or separately fabricated and assembled. For example, the tip 15 may be constructed of a thin film polymer or other material that is different from that selected for the substrate portion of a microfluidic chip. The tip may be subsequently assembled with the substrate portion and an adjoining outer layer in accordance with known fabrication methods such as those described in Kameoka et al, An Electrospray Ionization Source for Integration with Microfluidics, Anal. Chem.

2002, vol. 74, pp. 5897–5901, which is incorporated by reference herein in its entirety. The substrate portion may be formed with a relatively rectangular configuration having an end surface on which a separately etched or formed tip may be attached. The fluid channels formed along the substrate portion may be formed with apertures which lead up to the separately formed electrospray tip. The tip component can be formed separate and apart from the channel apertures, and thus, the microfluidic chip body may be formed with more than one channel each having a separate aperture that is coupled with others at a common tip region. For example, a triangular-shaped tip may be separately etched from a thin-film using lithographic techniques and positioned in alignment with the two or more microfluidic channels formed in the chip body. Alternatively, such thin film tips may be cut from polymers that are available in very thin films, such as polyimide (Kapton®) or polyester (Mylar®). These films may be cut using methods such as laser cutting or die cutting. The tip may serve as a fluid wick that protrudes from the edge of the microfluidic chip to provide an edge emitting ESI tip. The ESI tips provided in accordance with the invention assist in the formation of a relatively stable Taylor cone at the apex of the tip which provides an improved electrospray ionization source for analytical apparatus such as mass spectrometers. Alternatively, a substrate layer can be formed with a pointed distal tip portion with a relatively planar top surface on which a separate channel layer can be added to define the fluid channels. The channel layer may be etched by known techniques to form the plurality of fluid channels leading to the distal tip region. When it is preferable however to manufacture a single piece substrate, the ESI tip may be formed with a monolithic construction as a pointed extension protruding from the edge of the chip. Regardless of which manufacturing process is selected for forming the substrate portions of the ESI tips herein, a laminate or top layer may be bonded or otherwise attached to the substrate portion in order to enclose the fluid channels leading up to but excluding the converging distal tip region which should remain open-ended and exposed.

Figure 2:
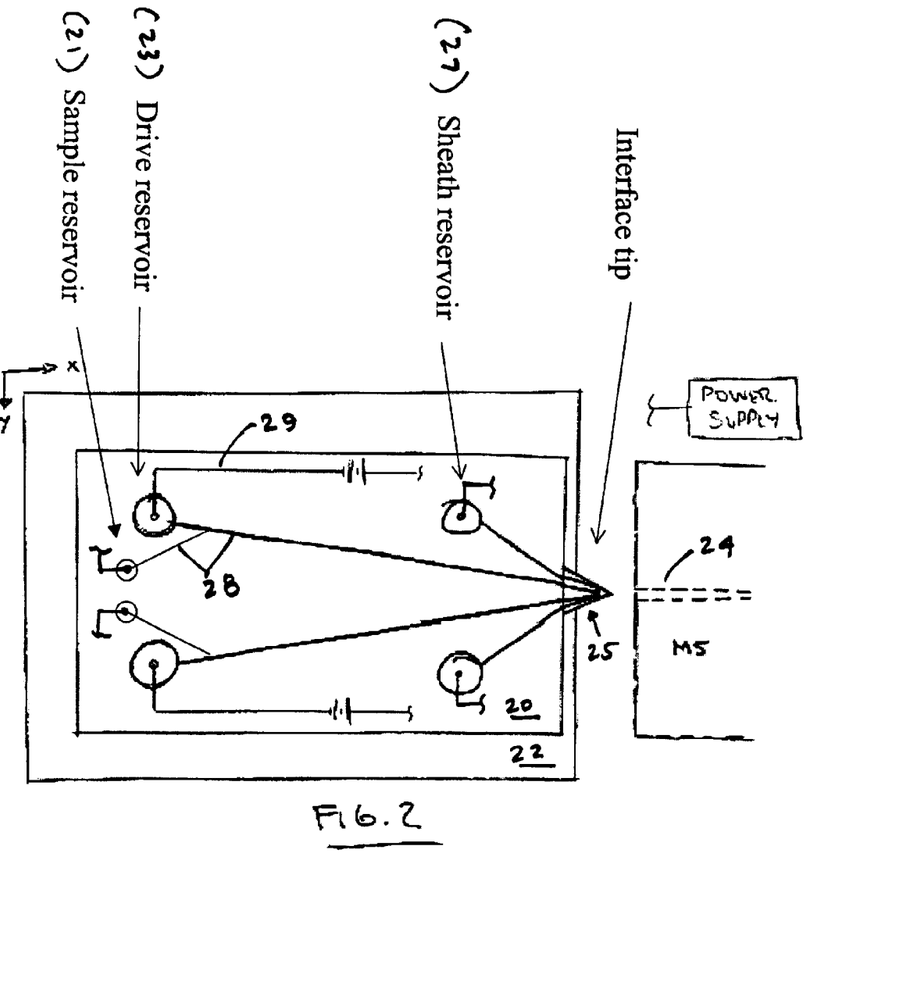
FIG. 2 is a simplified top view of a table mounted microfluidic chip that is formed with a tip for directing ionized spray into a neighboring mass spectrometer.

As shown in FIG. 2, the microfluidic devices provided in accordance with the invention can be incorporated into an ESI system for mass spectrometry analysis. A microfluidic chip 20 can be mounted as illustrated on a XY table or other adjustable platform 22 that is adjacent to a mass spectrometer (MS) such as an ABI Mariner time-of-flight (TOF) instrument. The table mounted microfluidic chip 20 can be formed with a tip 25 for directing ionized spray into the MS. The table 22 may be positioned and adjusted as needed to direct the device tip 25 and electrospray emissions into the capillary portion or receiving orifice 24 of the MS. In addition, the microfluidic chip 20 may be formed with one or more reservoirs that hold various fluids to be analyzed or run through the MS. The chip 20 may include a plurality of sample reservoirs 21, drive reservoirs 23 and sheath reservoirs 27. Each of the reservoirs may be fluidly and separately connected to a fluid channel or microchannel 28 formed within the chip body. An electrode 29 connected to a power source may be inserted into a reservoir so that a voltage is applied between the chip reservoir and MS. Electrodes may also be deposited and patterned on one of the polymer surfaces, preferably to contact the solution at the tip. A fluid pump may also be selected to impart the flow of fluids within the network of individual channels within the chip body. Each of the channels 28 within the body converge and lead to a common emitter tip 25 that also includes an enclosed portion that prevents cross-contamination of fluids. The emitter tip 25 however is also formed with a relatively open-distal tip portion that permits fluids originating from different reservoirs from within the chip body to emanate from a common ESI tip into a nearby MS for analysis. An improved ESI interface is thus provided in accordance with the invention that is different from previous arrangements including those with mass spectrometers directly connected to a microfluidic microchip.

An electrospray interface generally allows liquid substance specimens to be ionized before they are presented for mass spectrometry detection. Electrospray ionization generates ions for mass-spectroscopic analysis of various materials including chemical or biological specimens. The ESI process typically involves the emission of a liquid into a capillary at the input of a mass spectrometer from the spray tip that is subjected to an electrical potential having a range of values ranging from approximately 1–7 kV (kiloVolt). This potential can be controllably varied as part of a feedback loop to provide an electrospray with improved stability. The high electrical field generated thus induces charges on the surface of the liquid in the area of the spray tip. When this field is high enough, the liquid at the tip takes on the shape of a cone often referred to as a Taylor cone. The spraying of the fluid substance in the vicinity or area of the spray tip generally occurs when the Coulombic forces are great enough to overcome the surface tension forces present in the liquid. This spray occurs in the form of a thin jet of liquid at the tip of the Taylor cone. It has been observed that ionization by means of ESI for flow rates such as typically arise in microfluidic structures (10–1000 nl/min) do however require relatively high electrical field strengths. Accordingly, relatively fine spray tips with a diameter of about 10–100 $\mu$m are often required to cause ionization.

To carry out electrospray ionization mass spectrometry, the microfluidic chip 20 is positioned so that the distal end of an interface tip 25 is often placed a few millimeters (e.g., 1–4 mm) from the mass spectrometer (MS). The microfluidic chip 20 formed with an interface tip 25 in accordance with the invention as shown in FIG. 2 is positioned such that the interface tip is aligned with the MS. A sample is introduced into a sample introduction reservoir 21 using a suitable sampling device such as a micropipet or syringe. Furthermore, in order to carry out electrospray ionization process, a relatively high voltage and low current power supply can be selected to apply a voltage, e.g., 3–5 kV, with a driving reservoir electrode that can be inserted in the driving reservoir 21. Meanwhile, the sample introduction reservoir 21 is held at a lower voltage than driving reservoir 23 via a sample introduction reservoir electrode inserted in the sample introduction reservoir 21. For example, when a driving reservoir is held at 5 kV in one embodiment of the invention, a sample introduction reservoir is typically held at 6–7 kV. This drives the sample solution from a sample introduction reservoir through a distinct channel pathway towards a driving reservoir. Next, the power to the sample introduction reservoir may be turned off while the driving reservoir 23 is held a 5 kV, and in turn, a lower voltage than the driving reservoir is applied to a sheath liquid via an electrode inserted in the sheath liquid reservoir 27. The current path is from the driving reservoir 23 to the sheath liquid reservoir 27 via the interface tip 25. The sheath liquid reservoir 27 is held at 1–2 kV or ground. This drives the sample through its respective channel towards an outlet through the interface tip 25 and will eventually exit from an ESI tip opening formed with an open-end construction in accordance with an aspect of the invention. As the sample exits the tip opening, it is sprayed into the entrance capillary portion 24 of a mass spectrometer (MS) thus permitting its analysis. The voltage applied to the sheath liquid causes a Taylor cone to form at the interface tip 25 from which ions are generated by electrospray. The sheath liquid flow may be produced by applied pressure, electrokinetic flow or capillary action.

Figure 3A:
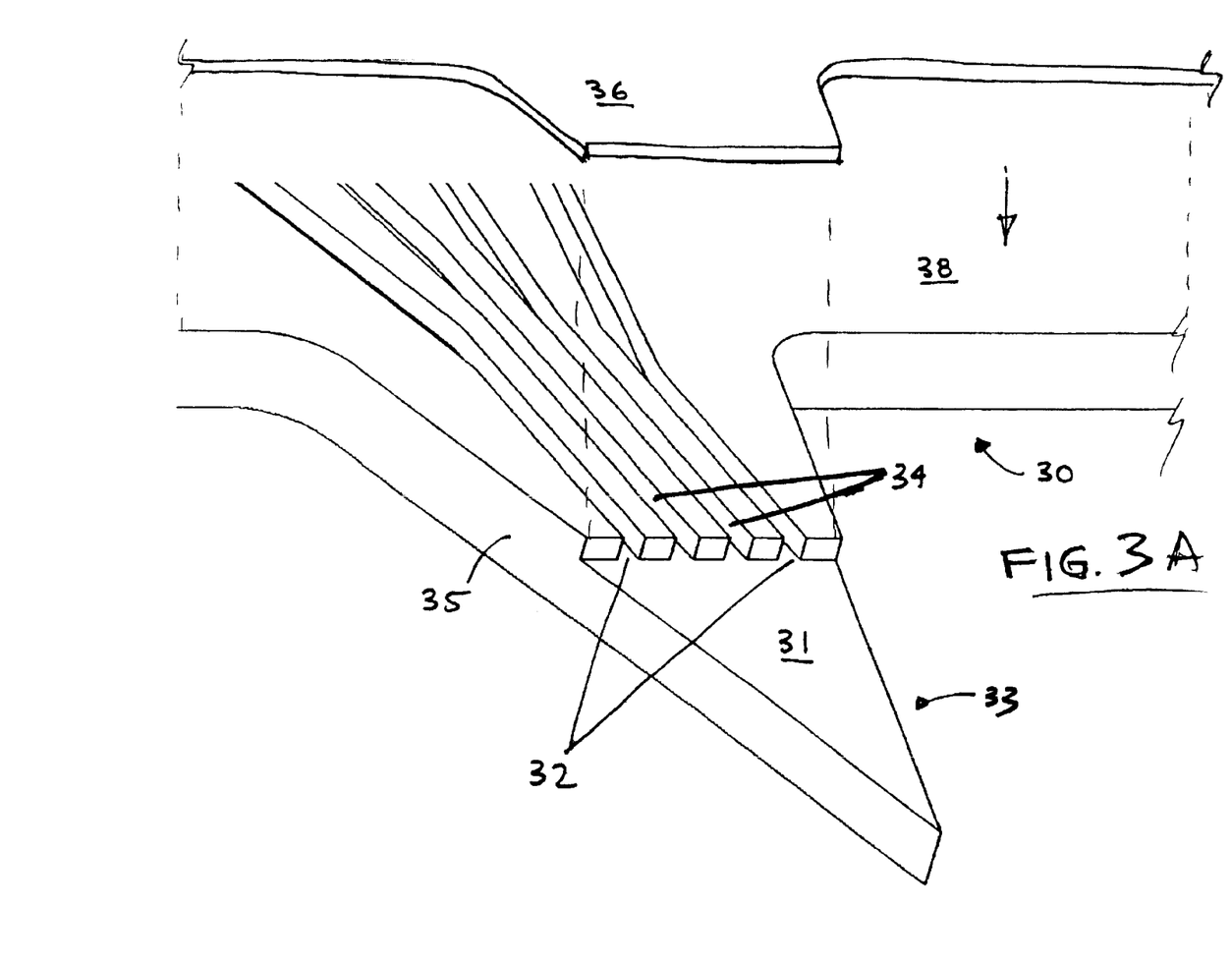
FIG. 3A is a perspective illustration of a microfluidic chip formed with a tip region and multiple fluid channels converging thereon.

As shown in FIG. 3A, another embodiment of the invention provides a partially exposed ESI tip 35 formed on a microfluidic chip 30 with multiple channels. The ESI tip channels may be formed by embossing techniques or other known processes to provide four or more separate converging channels. A pair of relatively outer channels 32 may be selected for a sheath flow to assist in the electrospray process, and a pair of relatively inner channels 34 may be used for a sample solution and a calibration solution. The plurality of channels can be formed along the microfluidic chip body in even-numbered pairs (2x) to provide 2, 4 or more fluid channels. The channels may converge at an embossed recessed tip 33 as shown to carry out microfluidic chip based ESI. It shall be understood however that the invention herein is not limited only to those embodiments illustrated and shall include electrospray devices formed with any even or odd-number of fluid microchannels leading to and converging at a open-ended distal tip.

Furthermore, the microfluidic chips provided herein may be formed by various embossing, molding, injection molding, or casting processes in accordance with the invention. These processes typically begin by etching a master in a material chosen to allow convenient and accurate microfabrication, such as glass or silicon. The etching is photolithographically patterned, and can use wet chemical etching, vapor phase etching methods, or plasma etching. One example of a method which yields good channel profiles is the deep reactive ion etching (DRIE) of silicon substrates. The master etched in this way can then either be directly replicated by the methods listed above, or a replica of the master may be made using an electroforming process, typically using nickel or a nickel alloy. One advantage of using an electroform is that it is more robust and less breakable than a glass or silicon wafer. It also inverts the surface profile. The electroform can then be used to make the final patterned device in the material of choice, typically a polymeric material that can be embossed, molded, or cast. There are also other materials, such as certain glasses that can be patterned by embossing or casting. The microchannels and the open-ended portion of the ESI tip shown in FIG. 3A may be formed with a two-depth etching process of a silicon master. This method may consist of at least two deep reactive ion etcher (DRIE) etching steps on a silicon master, each with its own lithographically defined masking pattern. The ESI tip may be formed by initially selecting a relatively thick polymeric layer ranging from approximately 0.5 to 2 mm in which the microchannels can be defined. A first etch step may be performed to create a multiple microfluidic channels that are etched to selected depths that can generally range from approximately 20 to 30 $\mu$m. A second etch step may be then completed to form open-end distal tip area that is etched to a selected depth that can range from approximately 100 to 300 $\mu$m. This second etch may extend to the edge of the microfluidic chip to define a sharp distal tip region where the microfluidic channels converge to provide a single multi-channel ESI tip. The three-dimensional patterning that is created by these multiple etches on a silicon master is then replicated into a polymeric substrate, through the intermediate of an electroform, as described above.

The microfluidic channels described herein may be further designed and fabricated by various known techniques and apparatus such as silicon master systems. A series of one or more channels may be formed with a predetermined depth following a methodology that can include the following steps: (1) defining a fluid channel design with a computer aided design (CAD) program, and constructing a photomask that is patterned after the selected design; (2) performing the photolithographic patterning of a photoresist layer on a silicon wafer or substrate using the constructed photomask; (3) etching the silicon in a deep reactive ion etcher (DRIE) to a selected depth such as 30 $\mu$m or greater to form channel structures with substantially straight sidewalls; (4) creating a negative version or electroform of this channel structure with nickel using techniques such as electroplating; (5) embossing the channel electroform into a sheet of polymer such as Zeonor at a relatively high temperature and selected pressure (Zeonor and other similar polymers may preferably have good solvent resistance and low water adsorption which are desired for mass spectroscopy applications); (6) forming or drilling well holes and fluid reservoirs into the polymer sheet as needed in relation to respective embossed channels; and (7) bonding a second, unpatterned, polymer sheet to the first sheet in order to enclose the channels. It shall be understood that other methods and variations of the preceding steps may be modified in accordance with the concepts of the invention. For example, it may be preferable to further treat the fluid channels with materials to improve observed performance characteristics. The channels may be modified in some instances to provide a more hydrophilic surface than can improve the electrospray performance of microfluidic devices. During the manufacturing process, a series of one or more open channels may be coated by slowly introducing a coating solution flowing from within the chip outward. An example of a suitable coating such as polyvinyl alcohol can be applied to the channel surfaces and thermally immobilized to remain in place for a sufficient period of time. By treating the channel surfaces in this manner, it may be possible to minimize or reduce protein adsorption and to prevent the emitted solutions from spreading to undesired portions of the microfluidic chip. A more stable and controlled electrospray may be thus provided as intended by the defined dimensions and configuration of a selected fluid channel.

The microfluidic chips provided in accordance with the invention herein may include an outer layer 36 formed of a relatively thin laminating film for enclosing the plurality of microchannels 32 and 34 as shown in FIG. 3A. This thin film layer 36 may be bonded or otherwise attached to a substrate layer 38 embossed with the convergent fluid microchannels. The converging microchannels may generally lead up to an open-tip region 31. The open-tip region 31 may be defined by a generally flat external surface formed on the substrate layer of the microfluidic chip. This region 31 can be formed by laminating the substrate layer 38 with a film 36 that is shaped and formed with dimensions so as to end just short of or at the base of the tip 33 as shown. A variety of preferably pointed configurations may be selected for the open-tip region 31, including a substantially triangular shape as illustrated. The outer layer 36 may be generally formed with a similar pattern as the substrate layer 38 but may extend only up to the base of the tip 33 thus forming an exposed area or open-tip region 31. The laminating cover layer 36 may thus cover over an underlying substrate polymer 38 to create a series of closed channels. For example, a top layer may consist of a thin sheet of Zeonor that may be bonded to the underlying substrate at lower values of temperature and pressure than when it is used as a selected material for embossing processes. The microfluidic chips herein may be laminated using a thin Zeonor film to seal the fluid channels that terminates near the base of the tip region. These tips provide open structures having a plurality converging channels that terminate with fluid openings intersecting at a common distal tip region. Various fluid materials may be thus directed through respectively defined fluid microchannels within the chip that lead up to and exit from a common distal tip.

With respect to the another embodiment of the invention that is also shown in FIG. 3A, some of the multiple converging fluid channels leading to the distal tip region of the microfluidic chip may be selected to introduce a sheath flow solution. A pair of outer microchannels 32 may be selected to introduce a sheath flow of organic solvent to optimize the electrospray process. In general, sheath flows are designed to assist during the electrospray process and are commonly used to couple conventional capillary electrophoresis (CE) instruments to mass spectrometry. A sheath flow provides numerous advantages including an ability to lessen the strict requirements on salt concentration, and fraction of organic solvent in CE separation. Since the electrospray process typically requires a constant flow of solution to achieve a suitable spray, a sheath flow may be provided to make up the difference when the CE separation is purely electrophoretic with no bulk flow of solution. In general, sheath flows typically use a mixture of aqueous buffers and non-aqueous solvents such as methanol, isopropanol, or acetonitrile. The advantages provided sheath flows can be similarly recognized when applied to microfluidic chips provided in accordance with the invention. Moreover, a sheath flow may be effective at relatively lower flow rates with some of the two-dimensional tip geometries described herein in comparison to those commonly used in conventional sheath flow interfaces. A 1:1 ratio of flow rates could be quite effective with the tip designs described herein, for example, as opposed to conventional sheath flow devices which often operate at 10:1 to 100:1 dilution ratios. The dilution of analyte with sheath flow designs provided in accordance with this aspect of the invention may be relatively minimal when compared to currently available sheath flow devices. Accordingly, the resulting loss of sensitivity can be greatly reduced with the low flow rates that can be achieved for the sheath flows generated by the microfluidic chips herein.

Figure 3B:
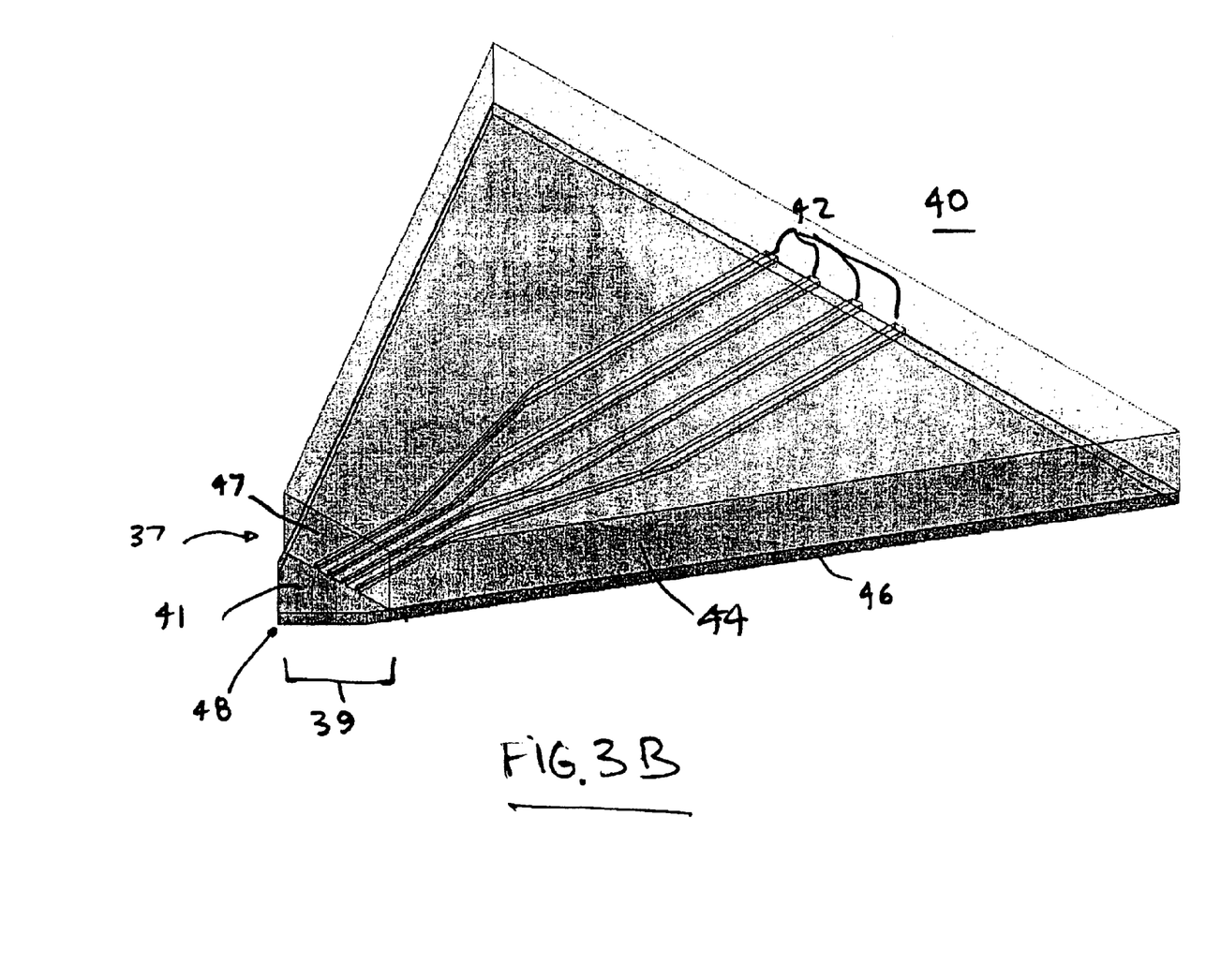
FIGS. 3B–C illustrate another embodiment of the invention formed with an extended substrate portion formed with an electrospray tip.
Figure 3C:
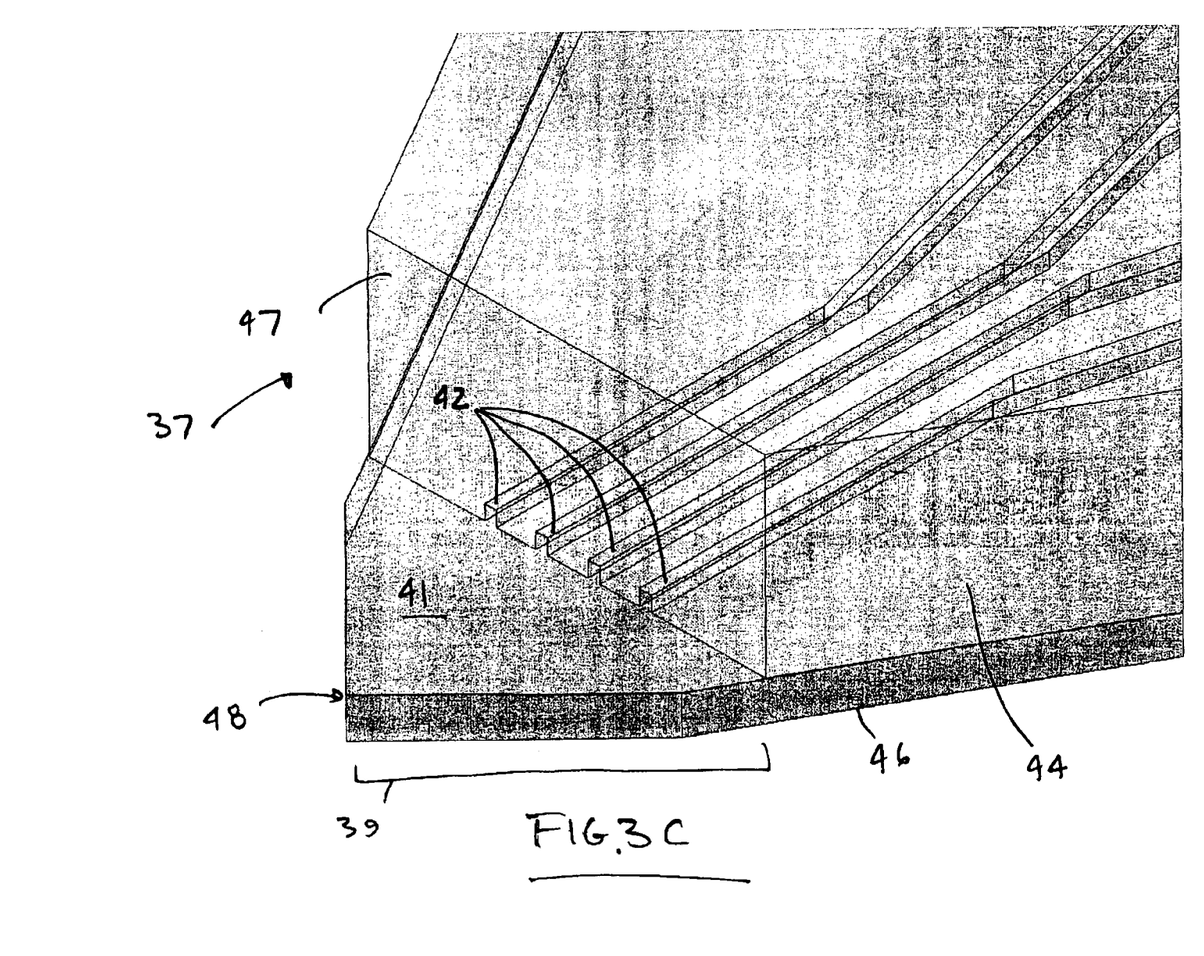

Another embodiment of the invention is shown in FIGS. 3B–C that provides an electrospray tip 37 formed with an extended substrate portion 39. As illustrated in FIG. 3B, a microfluidic chip 40 may include a plurality of channels 42 formed in a relatively thicker body layer 44 in accordance with fabrication methods described herein. A series of four channels with a substantially square shaped cross-section may be formed to direct various solutions to the ESI tip including samples and sheath fluids. FIGS. 3B–C further show that the ESI tip 37 may be formed with channels 42 running along a relatively bottom surface of the body layer 44 and terminating at a substantially flat end surface 47. In addition, a relatively thinner substrate layer 46 having a thickness of less than 1.0 mm can be bonded or laminated to the body layer 44 to enclose the channels 42. The substrate layer 46 includes an extended substrate portion 39 formed with a point 48 thus providing an exposed open-area region 41 for the ESI tip.

Figure 3D:
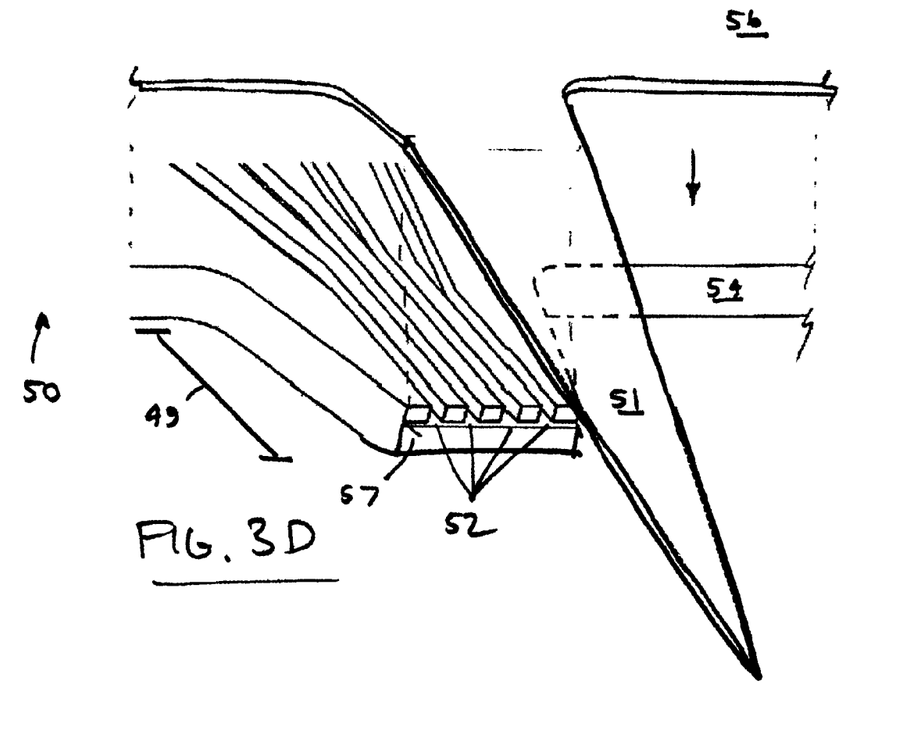
FIG. 3D is a perspective illustration of a microfluidic chip having an extended thin top layer forming an electrospray tip and a bottom layer terminating at a flat edge where multiple fluid channels end.
Figure 4A:
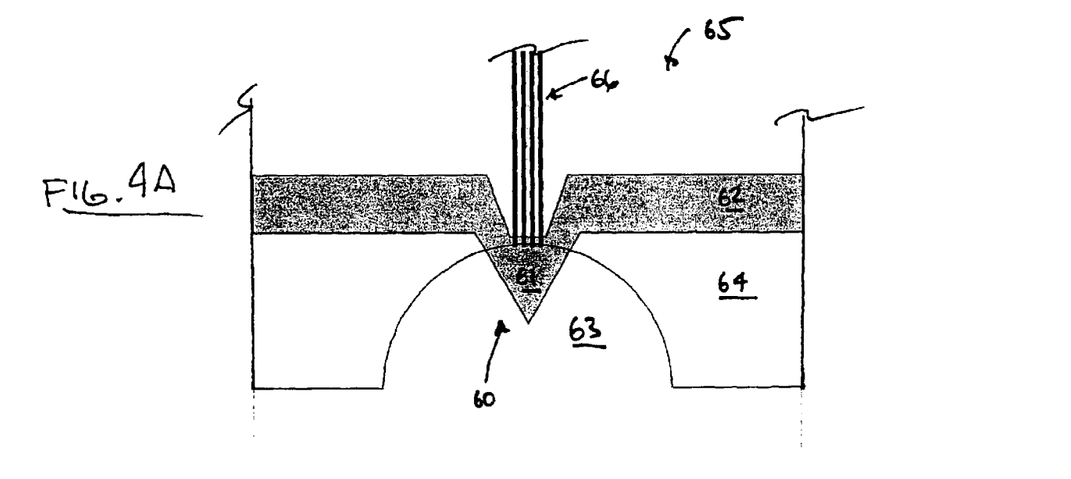
FIGS. 4A and 4B show another embodiment of the invention that provides a microfluidic chip formed with a recessed tip region.
Figure 4B:
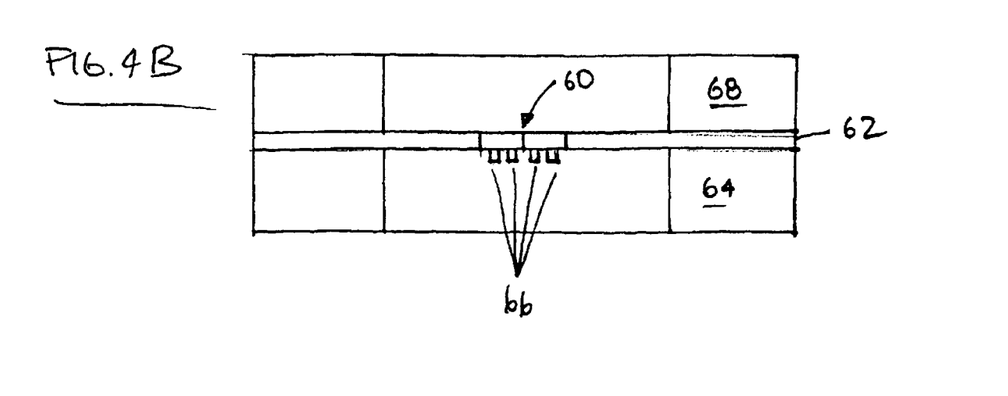

In accordance with yet another embodiment of the invention, a microfluidic chip 50 may be formed with an ESI tip having an extended top laminated layer 56 as shown in FIG. 3D. As with other variations of the invention provided herein, a substrate layer 54 may include a plurality of microchannels 52 which terminate at the substantially flat end surface 57 of a short substrate extension 49. The microchannels 52 can be formed along a relatively top surface of the substrate layer 54 and enclosed by the thin top laminate layer 56. The ESI tip may include a relatively thin lamination film having a thickness of less than 1.0 mm. The top layer 56 further includes a pointed tip portion 51 which extends beyond the edge of the relatively 54 thicker substrate layer in which channels 52 are embossed or otherwise formed. This embodiment of the invention may be formed as described above with respect to FIG. 3A except that the top layer 56 is not truncated but is rather formed with the pointed tip portion 51 extending past the flat end surface 57 of the substrate extension 49 at which the multiple fluid channels 52 terminate FIGS. 4A and 4B provide close-up views of another embodiment of the invention. FIG. 4A is the top view of an exposed edge-recessed ESI tip 60 that is fabricated from a thin metal-coated polymer film 62. The polymer film 62 is shown with a bottom polymer plate 64 in this illustration without a top laminate layer 68 so as to expose the interior region of the microfluidic device. In this embodiment of the invention, the microfluidic chip 65 includes a thin polymer film 62 that is placed along the edge of the chip body in a recessed area 63. A relatively open distal tip region 61 may protrude from the edge of the device 65 within the protected recessed area 63. A plurality of fluid channels 66 can be formed on a substrate layer 64 or polymer chip which run up to the edge of an opening at the edge of the chip 65. The recessed opening 63 along the edge of the chip may be drilled or otherwise formed with a desired geometric configuration such as a semi-circular pattern. The fluid channels 66 may be formed relatively close together with vertical sidewalls formed by an embossing process that starts with a DRIE etched silicon wafer, as discussed above. For example, a channel design may be selected with four channels each formed 20 $\mu$m wide and separated by 40 $\mu$m spaces in between. This configuration would only occupy a total width of 200 $\mu$m for all of the channels and wall spaces therebetween. Another embodiment of the invention may include the formation of 30 $\mu$m wide channels that are separated by 100 $\mu$m spaces. In this configuration, the total channel and wall width would be 420 $\mu$m wide. As observed in the semiconductor chip manufacturing industry, smaller lines widths generally require more demanding and exacting fabrication techniques. It shall be understood however that the relative spacing, width dimensions and the number of channels may be modified in accordance with the invention.

Another aspect of the invention provides a solution to the problem of creating ESI-emitting structures at the edge of a chip that are vulnerable to breakage. As shown in FIG. 4A, the tip structures 60 provided herein may be positioned within a recessed area 63 away from the edge in order to protect it. A recessed ESI tip has both practical and fabrication advantages. For example, the protected tip is often much less susceptible to breakage or contamination than one that protrudes from the chip. The end portion of a recessed channel that is fabricated by molding techniques achieves a generally more reliable edge rather than that formed by a cutting process which potentially results in the formation of burrs or small fragments of plastic. Based on the fabrication processes selected for prior designs, the recessed tips designs provided herein can be either injection molded or readily formed from a laser-cut polymeric platform. While both recessed and non-recessed ESI tips can be both formed with multiple convergent fluid channels leading to an open-ended distal tip described herein, either may be fabricated and comparatively tested to determine which configuration may provide a relatively more stable spray for certain applications. It shall be further understood that voltages may be similarly applied to drive fluid flow within microfluidic chips having recessed ESI tips as with other embodiments of the invention herein.

FIG. 4B illustrates the side view of the ESI tip 60 that is constructed from a thin polymer film 62 sandwiched and bonded in between two polymer plates 64 and 68. The thin polymer film 62 may be preferably formed of a very thin polymer having a thickness of approximately 10 microns that is sealed between the two relatively thicker polymeric layers 64 and 68. The thin metal-coated polymer film 62 may be selected and bonded to a substrate layer 64 as shown that includes four separate channels 66 leading up to and connected to the tip 60. A pair of relatively outer channels may be selected to provide a sheath flow to assist the electrospray process, and two relatively inner channels may be designated for spraying a sample fluid and a calibration solution, respectively. The sheath flow may be implemented as described elsewhere in this specification in accordance with the invention. It should be noted that the advantages of forming multiple channels leading to a single ESI tip are independent of whether the tip is recessed or not.

Figure 5A:
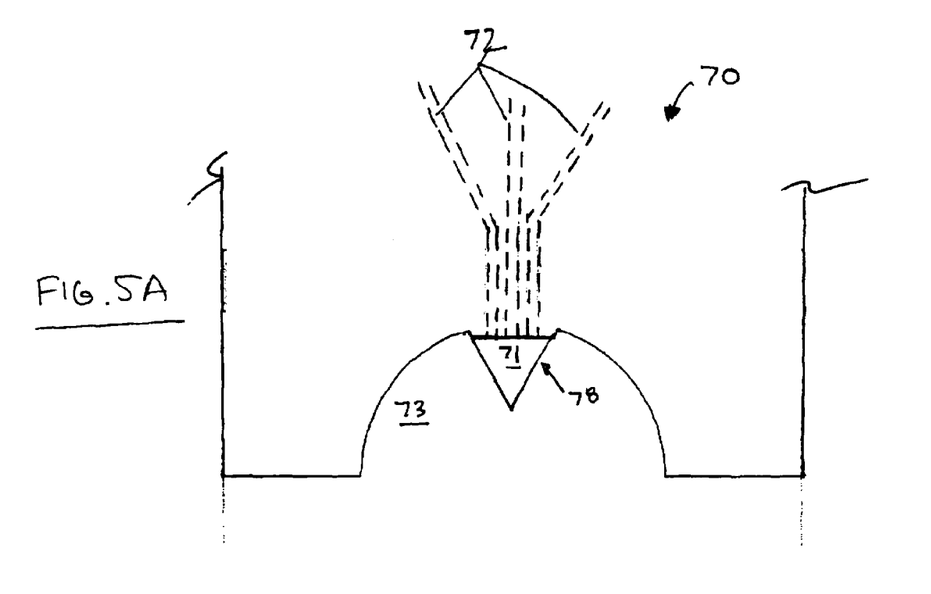
FIGS. 5A and 5B illustrate a microfluidic chip formed with a recessed tip integrally formed with a bottom polymer plate.
Figure 5B:
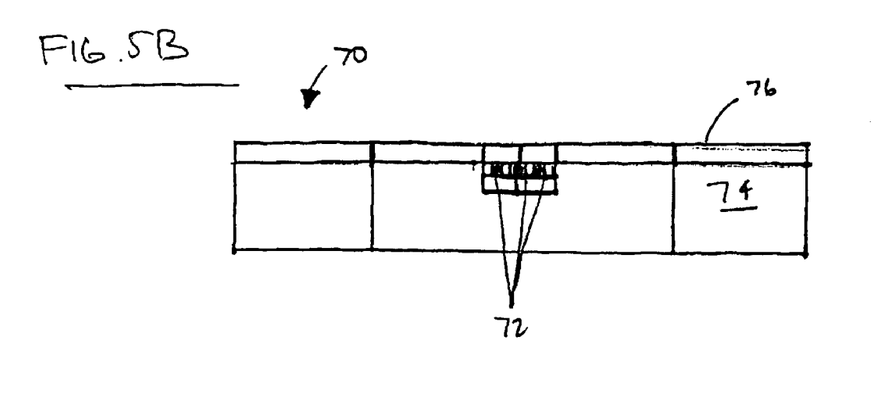

In yet another embodiment of the invention as shown in FIGS. 5A and 5B, a microfluidic chip 70 can be formed with a two-layer construction. The microfluidic chip 70 may include a polymer film layer 76 that encloses a series of one or more channels 72 formed in a bottom layer 74 as shown in FIG. 5A. A relatively open distal tip region 71 may protrude from the edge of the device 70 within the protected recessed area 73. The plurality of channels 72 formed in the bottom layer 74 of the chip 70 can extend up to the open distal tip region 71. Moreover, the recessed area 73 can be formed with a semicircular configuration as illustrated or some other type of arcuate shape. The distal tip region 71 may be formed with a pointed tip 78 that is protected within the recessed area 73. FIG. 5B illustrates a side view of the microfluidic chip 70 formed with two polymer plates 74 and 76. Rather than selecting a separate thin polymer film to form the ESI tip, one of the two polymer plates may be monolithically configured to provide the tip. In the illustrated embodiment, the bottom polymer layer 74 is formed with three separate channels 72 leading up to the electrospray tip 78. A pair of relatively outer channels 72 may be selected to provide a sheath flow to assist the electrospray process, and the relatively inner channel may be designated for spraying a sample fluid and a calibration solution, respectively. Alternatively, as with other variations of the invention provided herein, the outer channels may be selected to introduce one or more additional sample fluids.

Another aspect of the invention provides methods of creating recessed edge-emitting electrospray tips using a thin film of metal-coated polymer bonded in between two polymer layers. For example, a readily manufacturable fabrication process may include the step of forming a tip that is placed within a semi-circular recess to protect it. The fabrication process may employ commercially available laser-cutting apparatus to form and shape a thin film of metal-coated polymer as desired thus avoiding photolithography and etching processes. These thin films can be cut in very rapid succession in a cost-effective manner by laser apparatus such as a frequency-tripled YAG laser. The cutting process may thus take only a few seconds which are needed to cut the pattern for a selected chip. The metal coating of the thin film polymer may serve as the electrical contact to the ESI tip. The separate manufacturing step for the ESI tip may be incorporated with the overall assembly process for the microfluidic chips provided herein.

Figure 6:
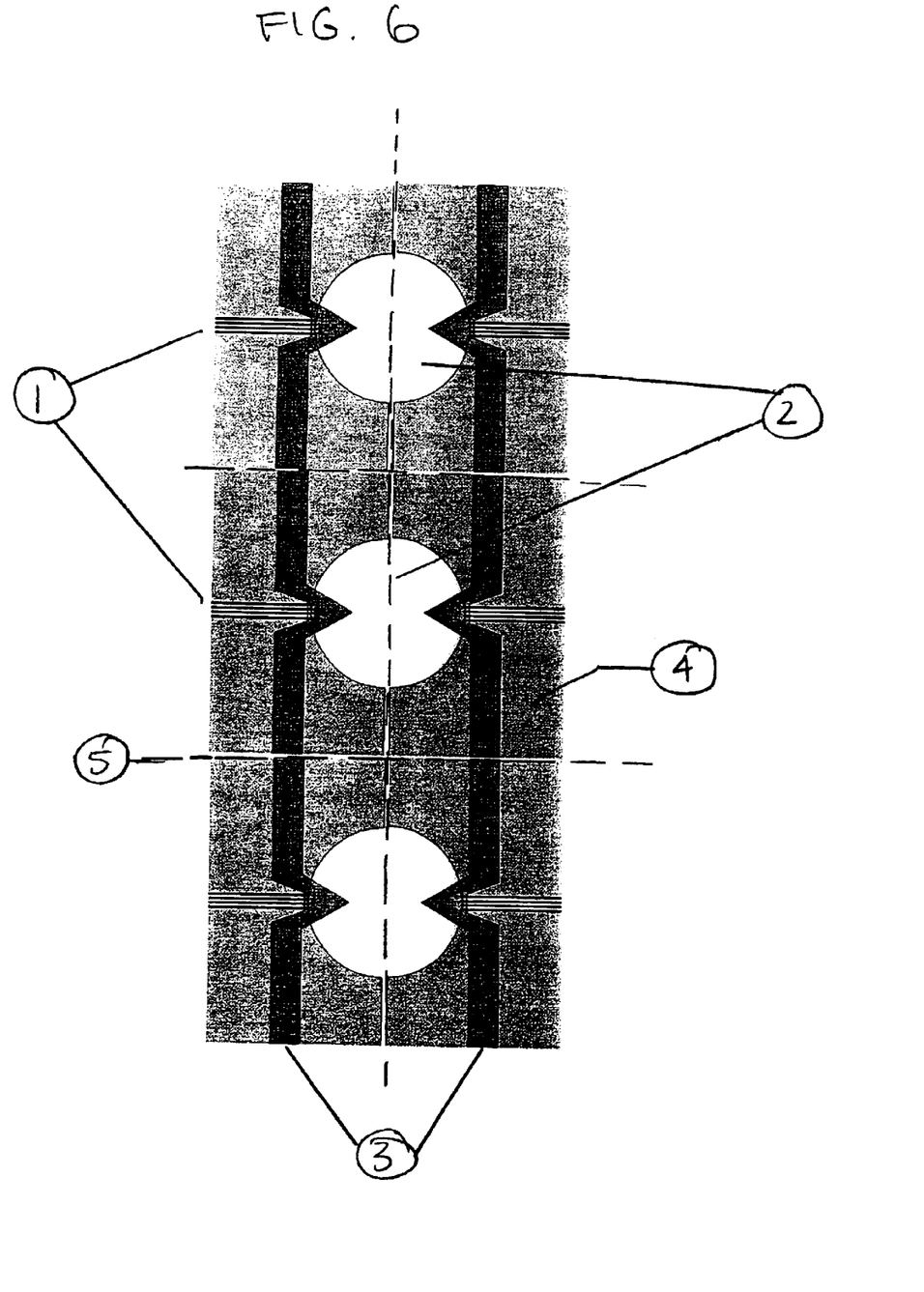
FIG. 6 is a diagram describing the manufacturing of microfluidic chips in batch quantities as provided by another aspect of the invention.

As shown in FIG. 6, a preferable method of manufacturing microfluidic chips in batch quantities is provided in accordance with another aspect of the invention, This method may be described as follows: (1) emboss the fluid channels for multiple microfluidic chips onto a polymer plate as described herein, including the formation of patterns at the edge of the chip for aligning two selected polymer plates; (2) drill a circular opening centered at the edge of each pair of adjacent chips along the polymer plates so that all of these openings can be drilled successively in the same operative step; (3) place a preformed strip of a laser-cut metal-coated polymer (see FIG. 4A) between the two plates that is aligned with the etched channel patterns—a single thin-film strip of a metal-coated polymer may be used for an entire row of adjacent chips on a plate; (4) thermally or otherwise bond the two polymer plates to seal the thin-film polymer (see FIG. 4B), preferably without distorting or flattening the cross-section of the embossed fluid channels; (5) separate the chips using CNC milling, sawing or die cutting techniques by forming cuts that go through the centers of the holes drilled earlier in Step (2). It shall be noted that these and other processes falling within the scope of the invention can be carried out on polymer plates which contain many chips. This can make chip fabrication cost-effective and substantially eliminate many of the time-consuming processes that are carried out on individual chips such as shaping the edges of each individual chip into a tip by machining processes. The microfluidic chips fabricated in accordance with this aspect of the invention offer many additional advantages over conventional devices that are embodied in a single microfluidic chip, including but not limited to following: (a) a tip that may be recessed and protected from mechanical damage; (b) a tip that may be metal-coated thus conveniently providing an electrical contact for electrospray ionization; (c) a plurality of fluid channels terminating at a single common ESI tip for emission of multiple fluids and samples; (d) etched alignment features that may be used to accurately align the thin polymer plates to form the microfluidic chips; and (e) a single laser-cut strip of metalcoated thin-film polymer used during a fabrication process that is sandwiched in between polymer plates for the production of entire rows of microfluidic chips.

While the invention has been described with reference to the aforementioned specification, the descriptions and illustrations of the preferable embodiments herein are not meant to be construed in a limiting sense. It shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art upon reference to the present disclosure. It is therefore contemplated that the appended claims shall also cover any such modifications, variations and equivalents.

What is claimed is:

1. A microfluidic chip for mass spectrometric analysis comprising:
   a microfluidic body formed with a plurality of reservoirs for containing at least one fluid medium;
   a plurality of separated channels formed within the microfluidic body that are in fluid communication with a corresponding reservoir but are not in fluid communication with each other within at least a portion of the microfluidic body; and
   an electrospray ionization tip formed with an open-ended distal tip portion that is positioned along an end surface of the microfluidic body, wherein the plurality of separated channels converge at the open-ended distal tip portion to direct an ionization spray derived from the fluid mediums.

2. The apparatus as recited in claim 1, wherein the open-ended distal tip portion of the electrospray ionization tip includes a layer of hydrophilic material.

3. The apparatus as recited in claim 1, further comprising:

a top laminate layer for enclosing the plurality of separated channels formed within the microfluidic body except for the open-ended distal tip portion of the microfluidic body.

4. The apparatus as recited in claim 1, wherein the microfluidic body is formed of a material selected from one of the following: a polymer, a copolymer, an elastomer, a ceramic, quartz, silicon, silicon dioxide, silica, and glass.

5. A microfluidic chip for electrospray ionization comprising:

a bottom polymer plate formed with at least two non-intersecting fluid channels that are each in fluid communication with corresponding fluid reservoirs included within the polymer plate;

an electrospray tip positioned within a recessed portion formed in the bottom polymer plate, wherein the electrospray tip includes an open-tip region at which each of the non-intersecting fluid channels converge; and a top polymer plate that substantially encloses the non-intersecting fluid channels formed in the bottom polymer plate except for the open-tip region of the electrospray tip.

6. The microfluidic chip as recited in claim 5, wherein the electrospray tip is formed with a sharp point that is protected within the recessed portion formed in the bottom polymer plate.

7. A method for conducting mass spectrometric analysis of multiple samples in a sequential manner comprising the following steps of:

selecting a microfluidic chip formed with a electrospray tip, wherein the microfluidic chip includes a plurality of fluid channels that converge at an open-end distal portion of the electrospray tip;

positioning the electrospray tip relative to a mass spectrometer for analysis of multiple samples;

introducing a first sample through a first fluid channel within the microfluidic chip that directs an electrospray of the first sample emanating from the open-end distal portion of the electrospray tip into the mass spectrometer;

conducting a mass spectrometric analysis of the first sample;

introducing a second sample through a second fluid channel within the microfluidic chip that directs an electrospray of the second sample emanating from the open-end distal portion of the electrospray tip into the mass spectrometer;

conducting a mass spectrometric analysis of the second sample, wherein the mass spectrometric analysis of the first sample and the second sample are conducted sequentially from the same electrospray tip formed on the microfluidic chip.

8. The method as recited in claim 7, further comprising the step of:

introducing a calibration solution through a third channel within the microfluidic chip that directs an electrospray of the calibration solution emanating from the open-end distal portion of the electrospray tip into the mass spectrometer.

9. The method as recited in claim 7, further comprising the step of:

introducing a calibration solution through the first or second channel within the microfluidic chip that directs an electrospray of the calibration solution emanating from the open-end distal portion of the electrospray tip into the mass spectrometer.

10. The method as recited in claim 7, further comprising the step of:

introducing a sheath flow through a single or a pair of relatively outer channels through the microfluidic chip that directs an electrospray of the sheath flow emanating from the open-end distal portion of the electrospray tip into the mass spectrometer.

11. The method as recited in claim 10, wherein the sheath flow is simultaneously introduced with either the introduction of the first sample or the second sample.

12. The method as recited in claim 10, the sheath flow is introduced using electrokinetic forces or by application of fluidic pressure.

* * * * *

UNITED STATES PATENT AND TRADEMARK OFFICE
CERTIFICATE OF CORRECTION

PATENT NO. : 6,803,568 B2
DATED : October 12, 2004
INVENTOR(S) : Luc Bousse et al.

It is certified that error appears in the above-identified patent and that said Letters Patent is hereby corrected as shown below:

<u>Title page,</u>
Delete Item "[30] Foreign Application Priority Data,
            Sep. 19, 2001 (DE) ………………….. 101 46 286".

Signed and Sealed this

Sixth Day of September, 2005

JON W. DUDAS
*Director of the United States Patent and Trademark Office*